United States Patent
Lathim

(10) Patent No.: US 8,832,901 B2
(45) Date of Patent: Sep. 16, 2014

(54) HAND-OPERABLE VACUUM DEVICE

(71) Applicant: Del Lathim, Pasco, WA (US)

(72) Inventor: Del Lathim, Pasco, WA (US)

( * ) Notice: Subject to any disclaimer, the term of this patent is extended or adjusted under 35 U.S.C. 154(b) by 0 days.

(21) Appl. No.: 14/056,692

(22) Filed: Oct. 17, 2013

(65) Prior Publication Data

US 2014/0090202 A1    Apr. 3, 2014

Related U.S. Application Data

(63) Continuation of application No. 12/983,178, filed on Dec. 31, 2010, now Pat. No. 8,584,311.

(60) Provisional application No. 61/362,240, filed on Jul. 7, 2010.

(51) Int. Cl.
  *A61M 1/00*    (2006.01)

(52) U.S. Cl.
  CPC .......... *A61M 1/003* (2013.01); *A61M 2210/065* (2013.01); *A61M 1/0086* (2014.02); *A61M 2210/0618* (2013.01); *A61M 1/0072* (2014.02); *A61M 2205/075* (2013.01); *A61M 1/0066* (2013.01)
  USPC ................................. 15/344; 604/37; 15/405

(58) Field of Classification Search
  CPC ............ A61M 1/0003; A61M 1/0066; A61M 1/0072; A61M 2205/075; A61M 2210/0618
  USPC ............ 15/344; 222/206, 213, 214; 228/20.5; 604/212, 319, 37, 94.01
  See application file for complete search history.

(56) References Cited

U.S. PATENT DOCUMENTS

| | | | | |
|---|---|---|---|---|
| 764,996 A | * | 7/1904 | Ellis | 604/37 |
| 1,469,764 A | * | 10/1923 | Crisenberry | 604/37 |
| 1,660,085 A | * | 2/1928 | Elnain | 222/78 |
| 1,668,895 A | * | 5/1928 | Fulton | 222/213 |
| 2,511,469 A | * | 6/1950 | Hawks | 604/185 |
| 3,618,846 A | * | 11/1971 | Poli | 228/52 |
| 3,902,364 A | * | 9/1975 | Craig et al. | 73/160 |
| 4,258,714 A | * | 3/1981 | Leopoldi et al. | 604/118 |
| 4,405,321 A | * | 9/1983 | Budoff | 604/212 |
| 4,564,129 A | * | 1/1986 | Urban et al. | 222/207 |
| D305,262 S | * | 12/1989 | Nichols | D24/115 |
| 4,898,306 A | * | 2/1990 | Pardes | 222/206 |
| 5,114,415 A | * | 5/1992 | Shedlock | 604/319 |
| 5,270,054 A | * | 12/1993 | Bertolini | 424/451 |
| 5,290,257 A | * | 3/1994 | Zhong | 604/212 |
| 5,720,330 A | * | 2/1998 | Schmalz, Jr. | 141/26 |
| 6,619,516 B2 | * | 9/2003 | Weiler et al. | 222/420 |
| 6,875,201 B1 | * | 4/2005 | Kawashima et al. | 604/295 |
| 7,562,796 B2 | * | 7/2009 | Zahn et al. | 222/541.9 |
| 2011/0139149 A1 | * | 6/2011 | Cacka et al. | 128/200.14 |

* cited by examiner

*Primary Examiner* — Lee D Wilson
*Assistant Examiner* — Tyrone V Hall, Jr.
(74) *Attorney, Agent, or Firm* — Rainier Patents, P.S.; Paul W. Mitchell; Remembrance L. Newcombe

(57) ABSTRACT

This patent relates to devices that can be manipulated by a user to expel or draw in a material. In one example, a hand-operable vacuum device can include an interface portion configured to contact a material. The hand-operable vacuum device can also include a deformable portion that extends along an axis that passes through the interface portion and wherein the deformable portion includes at least one longitudinally-oriented resilient structure that extends generally parallel to the axis.

11 Claims, 9 Drawing Sheets

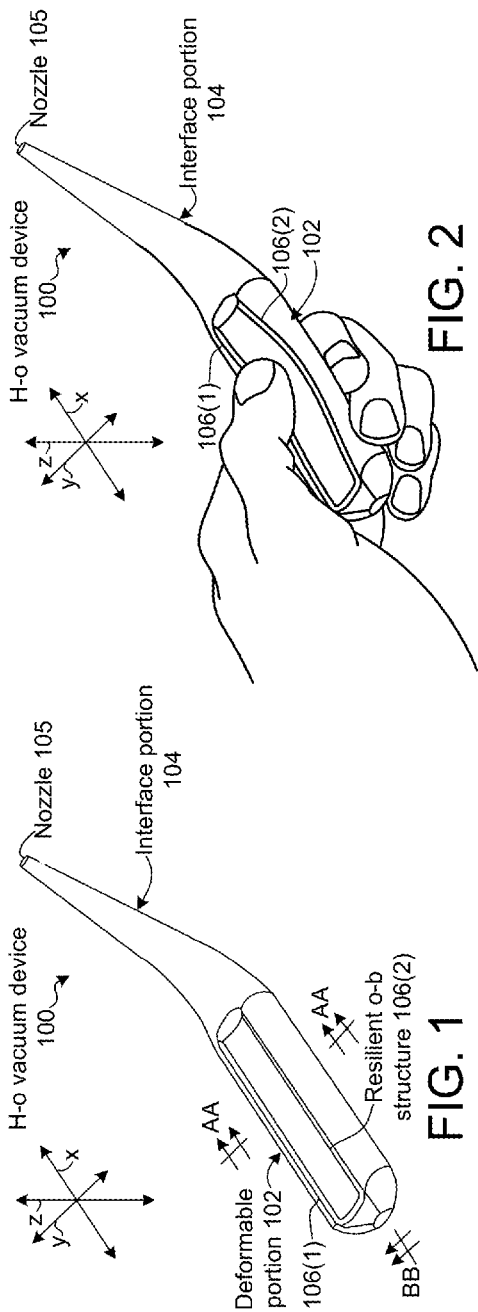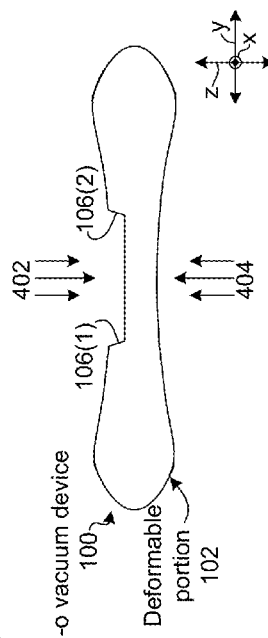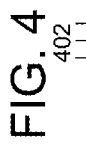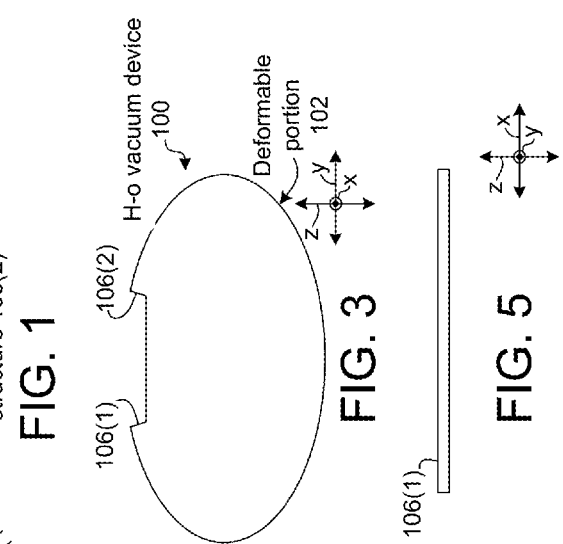

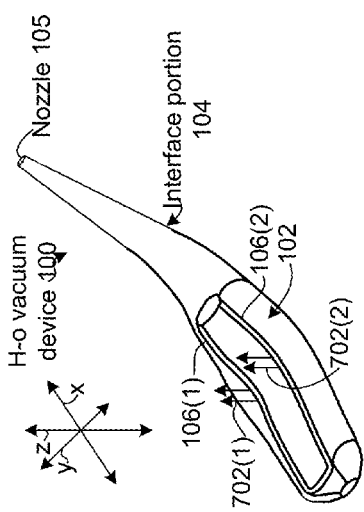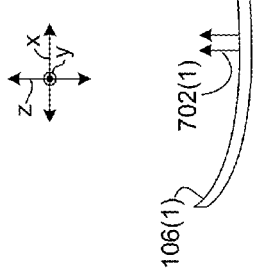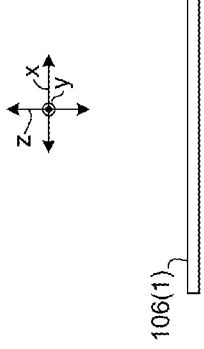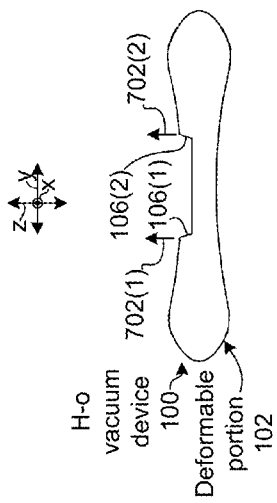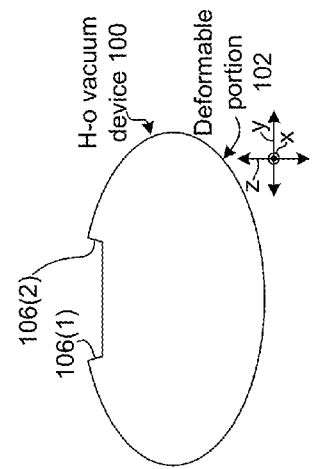

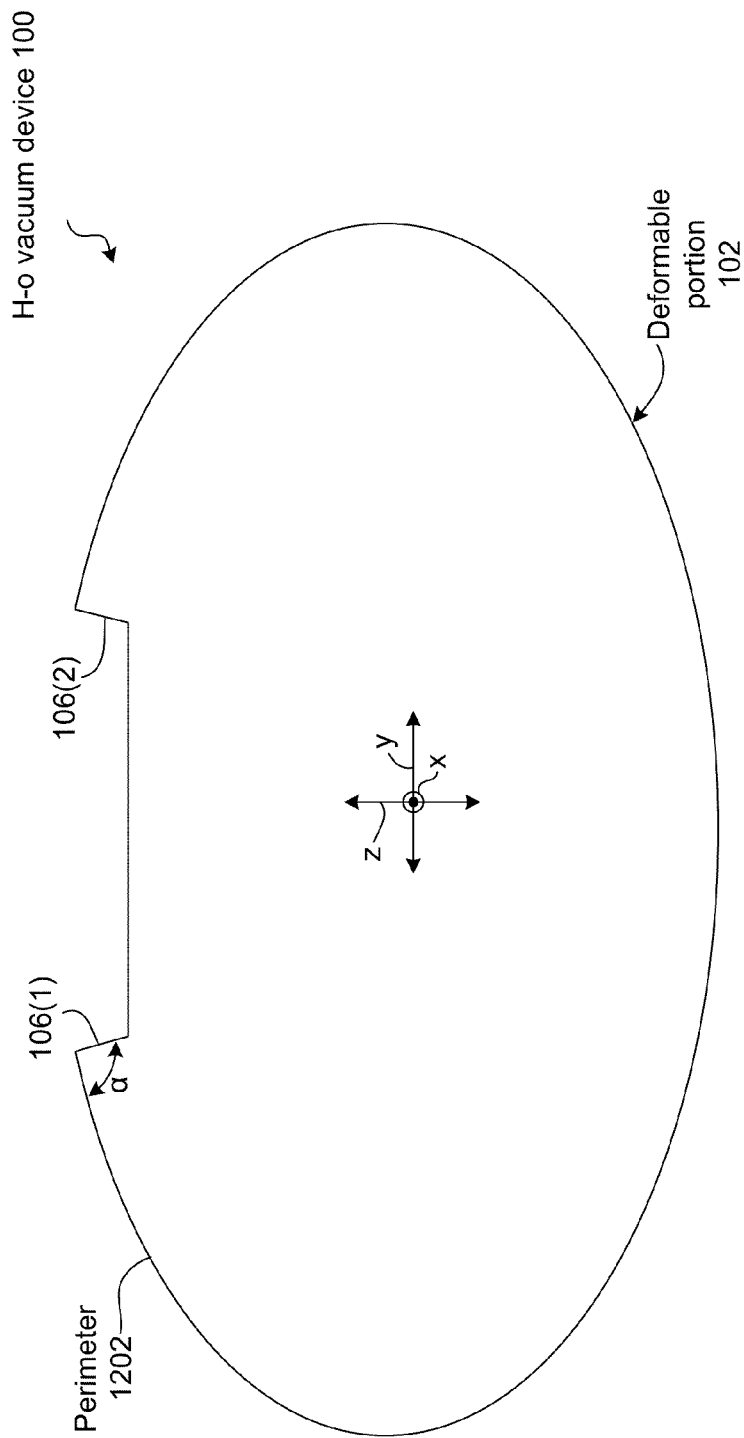

H-o vacuum device 1700

H-o vacuum device 1800

H-o vacuum device 1900

HAND-OPERABLE VACUUM DEVICE

PRIORITY

This Utility Application is a continuation of and claims priority from U.S. patent application Ser. No. 12/983,178 and U.S. Provisional Application No. 61/362,240, which are hereby incorporated by reference.

BRIEF DESCRIPTION OF THE DRAWINGS

The accompanying drawings illustrate implementations of the concepts conveyed in the present application. Features of the illustrated implementations can be more readily understood by reference to the following description taken in conjunction with the accompanying drawings. Like reference numbers in the various drawings are used wherever feasible to indicate like elements. Further, the left-most numeral of each reference number conveys the figure and associated discussion where the reference number is first introduced (where feasible).

FIGS. 1-2 and 7 are perspective views of an example of a hand-operable vacuum device in accordance with some of the present concepts.

FIGS. 3-6 and 8-12 are sectional views of a portion of a hand-operable vacuum device in accordance with some of the present concepts.

DETAILED DESCRIPTION

Overview

Figure 13:
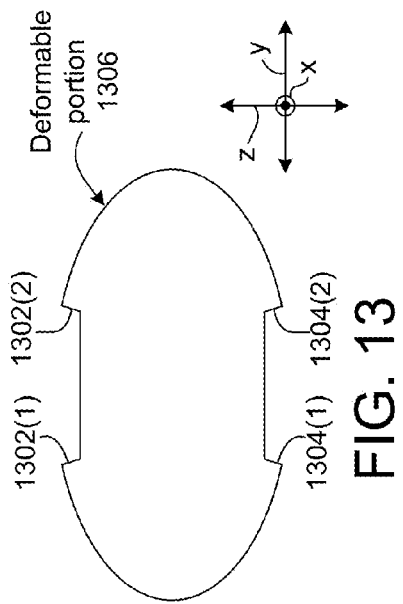
FIGS. 13-15 are sectional views of a portion of hand-operable vacuum devices in accordance with some of the present concepts.

The present description relates to hand-operable vacuum devices. In some cases, hand-operable vacuum devices can be manipulated by a user to draw material into the device and/or expel material from the device. The hand-operable vacuum device can be constructed such that a user can squeeze and deform the device and then the device is resiliently biased to return to an original configuration. The construction of the hand-operable vacuum device can include generally longitudinally arranged resilient outwardly-biasing structures that bias the device back to its original configuration more effectively than existing technologies. This effective bias can create relatively strong vacuum forces for drawing material into the hand-operable vacuum device.

Examples

FIGS. 1-11 collectively show an example of a hand-operable vacuum device 100. FIGS. 1, 3, and 5 show the hand-operable vacuum device 100 in a first configuration. FIGS. 2, 4, and 6 show the hand-operable vacuum device 100 manipulated into a second configuration by a human user. FIGS. 7-11 collectively show how the construction of the hand-operable vacuum device 100 promotes returning to the first configuration of FIGS. 1, 3, and 5 when the user stops manipulating the device. Briefly, the hand-operable vacuum device 100 can be resiliently biased to assume and/or return to the first configuration after user manipulation.

FIGS. 1 and 2 show perspective views of the hand-operable vacuum device. FIGS. 3-4 show sectional views of the hand-operable vacuum device taken along section AA indicated in FIG. 1. Section AA is transverse to the x-reference axis and parallel to the yz-reference plane. FIGS. 5-6 show a component of the hand-operable vacuum device taken parallel to the xz-reference plane as indicated along section BB.

In some cases, the hand-operable vacuum device 100 can be thought of as having a deformable portion 102 and an interface portion 104 that can include a nozzle 105. The deformable portion 102 can extend along a long axis that runs parallel to the x-reference axis. The deformable portion can be generally elongated, spherical, or other shape. The deformable portion can include one or more resilient outwardly-biasing structures 106. In some implementations the resilient outwardly-biasing structures can be longitudinally oriented (i.e., parallel to the long axis). In this case, the hand-operable vacuum device includes a pair of resilient outwardly-biasing structures 106(1) and 106(2).

The deformable portion 102 can be manipulated or squeezed by a user as indicated by arrows 402 and 404 to deform or squish the deformable portion. The squishing can bend the resilient outwardly-biasing structures as can be seen by comparing FIGS. 5 and 6 which show resilient outwardly-biasing structure 106(1). FIG. 5 shows the resilient outwardly-biasing structure in a resting or biased configuration. FIG. 6 shows a bowed configuration of the resilient outwardly-biasing structure produced by user manipulation.

FIGS. 7-11 show how the resilient outwardly-biasing structures 106(1) and 106(2) can return the deformable portion 102 to the resting configuration when the user stops applying pressure. Specifically, upward arrows 702(1) and 702(2) indicate the outward bias exerted by resilient outwardly-biasing structures 106(1) and 106(2), respectively. The outward bias returns the resilient outwardly-biasing structures from the bowed configuration of FIG. 8 to the more linear configuration of FIG. 9. (In another implementation, the resilient outwardly-biasing structures could be outwardly bowed at rest such that user manipulation causes them to be less bowed.) The outward bias exerted by resilient outwardly-biasing structures 106(1) and 106(2) facilitates returning the deformable portion from the manipulated configuration of FIG. 10 to the resting configuration of FIG. 11. Returning the deformable portion to the resting configuration can increase the volume thereof and can thereby create a very strong vacuum that can be utilized to draw material into the interface portion 104 via nozzle 105.

FIG. 12 illustrates an example of how the resilient outwardly-biasing structures 106(1) and 106(2) can extend from a perimeter 1202 of the deformable portion 102. In various implementations the resilient outwardly-biasing structures can extend from the perimeter at an angle α that is oblique or a right angle relative to the perimeter proximate to the outwardly-biasing structure. In some implementations, the angle α can be in a range from about 90 degrees to about 135 degrees. Other implementations may be outside this range.

Figure 14:
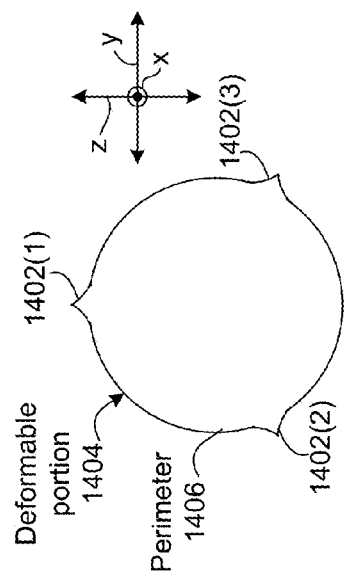

The example implementations above include a pair of outwardly-biasing structures 106(1) and 106(2). FIGS. 13-14 illustrate some alternative implementations of hand-operable vacuum devices.

FIG. 13 shows first and second pairs of outwardly-biasing structures 1302(1), 1302(2) and 1304(1), 1304(2) on deformable portion 1306. In this example the first and second pairs are generally opposing one another, but such need not be the case. However, the present example can be useful in facilitating the user's grip.

FIG. 14 shows an alternative implementation that includes three outwardly-biasing structures 1402(1), 1402(2), and 1402(3) on deformable portion 1404. In this case the outwardly-biasing structures extend outwardly from perimeter 1406 rather than inwardly as illustrated in the example implementations of FIGS. 1-13.

Figure 15:
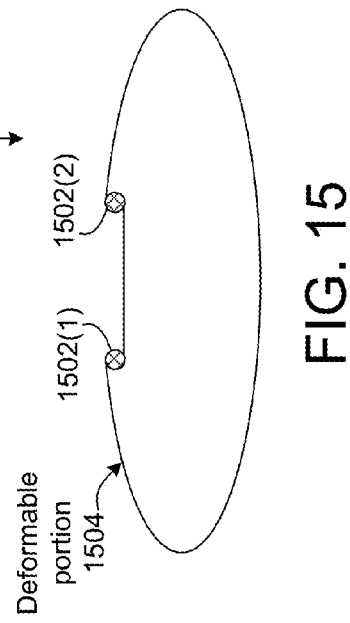

FIG. 15 offers another implementation with two outwardly-biasing structures 1502(1) and 1502(2) on deformable portion 1504. In this case, the outwardly-biasing structures are generally elliptical rather than linear when viewed in cross-section. Other shapes and/or configurations can alternatively or additionally be utilized.

Figure 16:
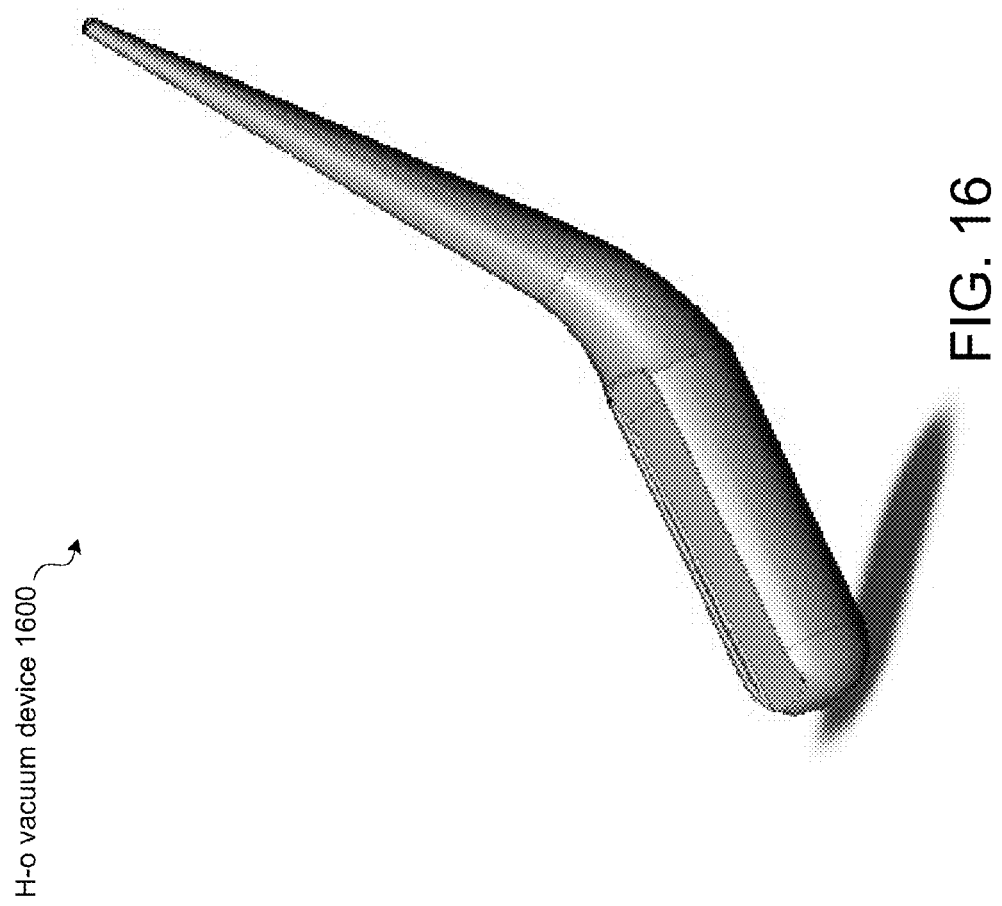
FIGS. 16-19 are perspective views of examples of hand-operable vacuum devices in accordance with some of the present concepts.

FIG. 16 shows an example hand-operated vacuum device 1600 that can be employed as a specimen collector, among other uses.

Figure 17:
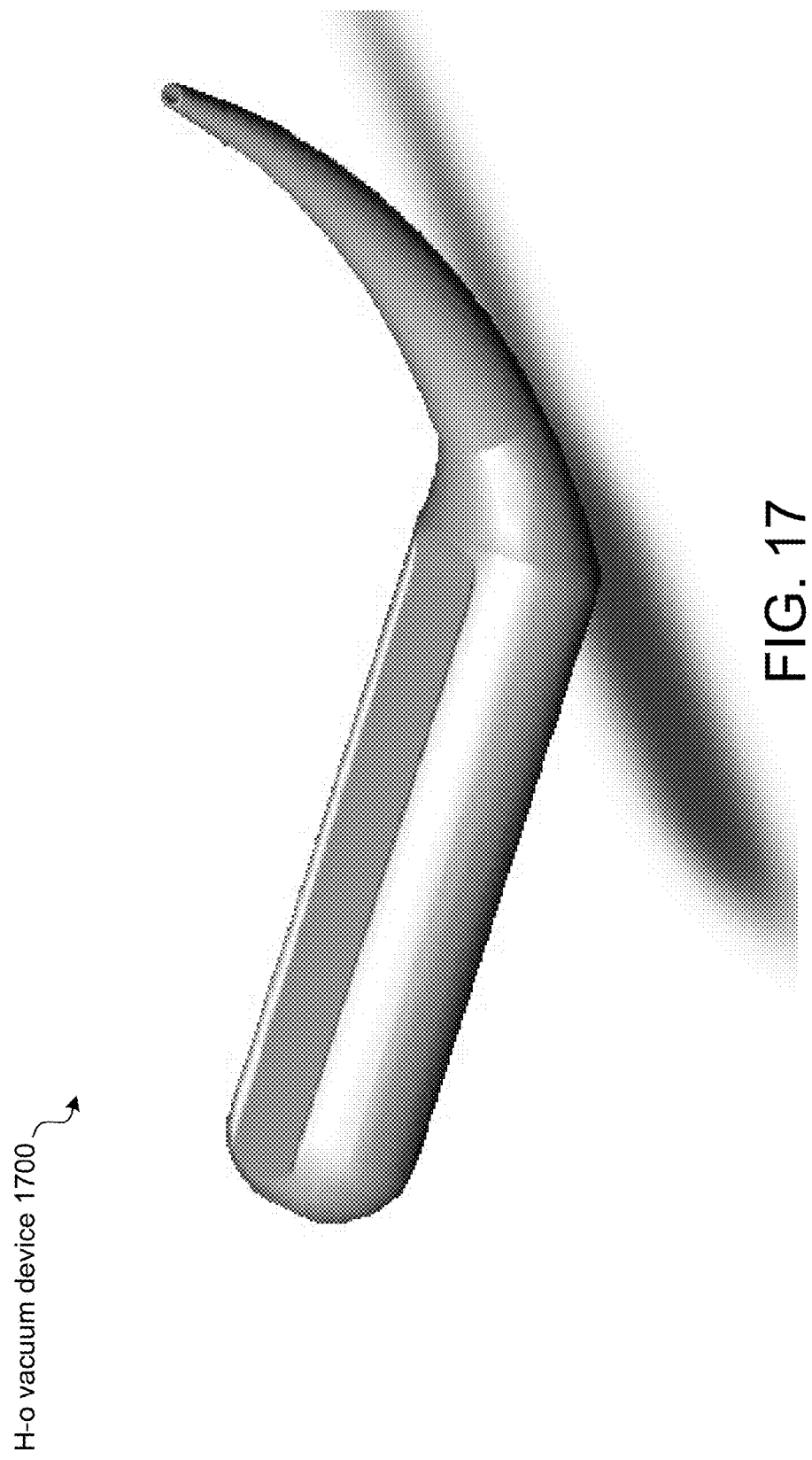

FIG. 17 shows an example hand-operated vacuum device 1700 that can be employed as a throat aspirator, among other uses.

Figure 18:
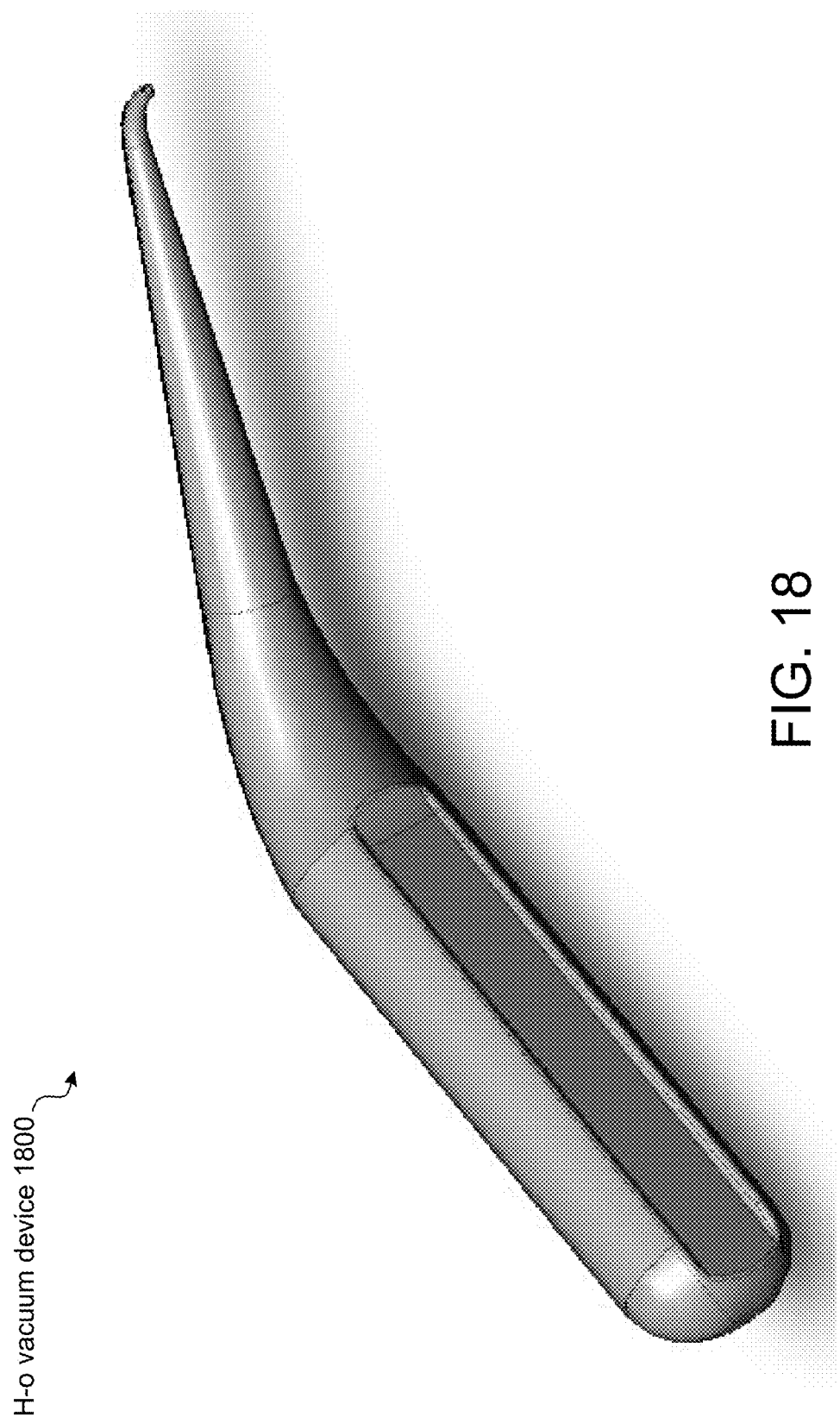

FIG. 18 shows an example hand-operated vacuum device 1800 that can be employed as a dental squirt pick, among others.

Figure 19:
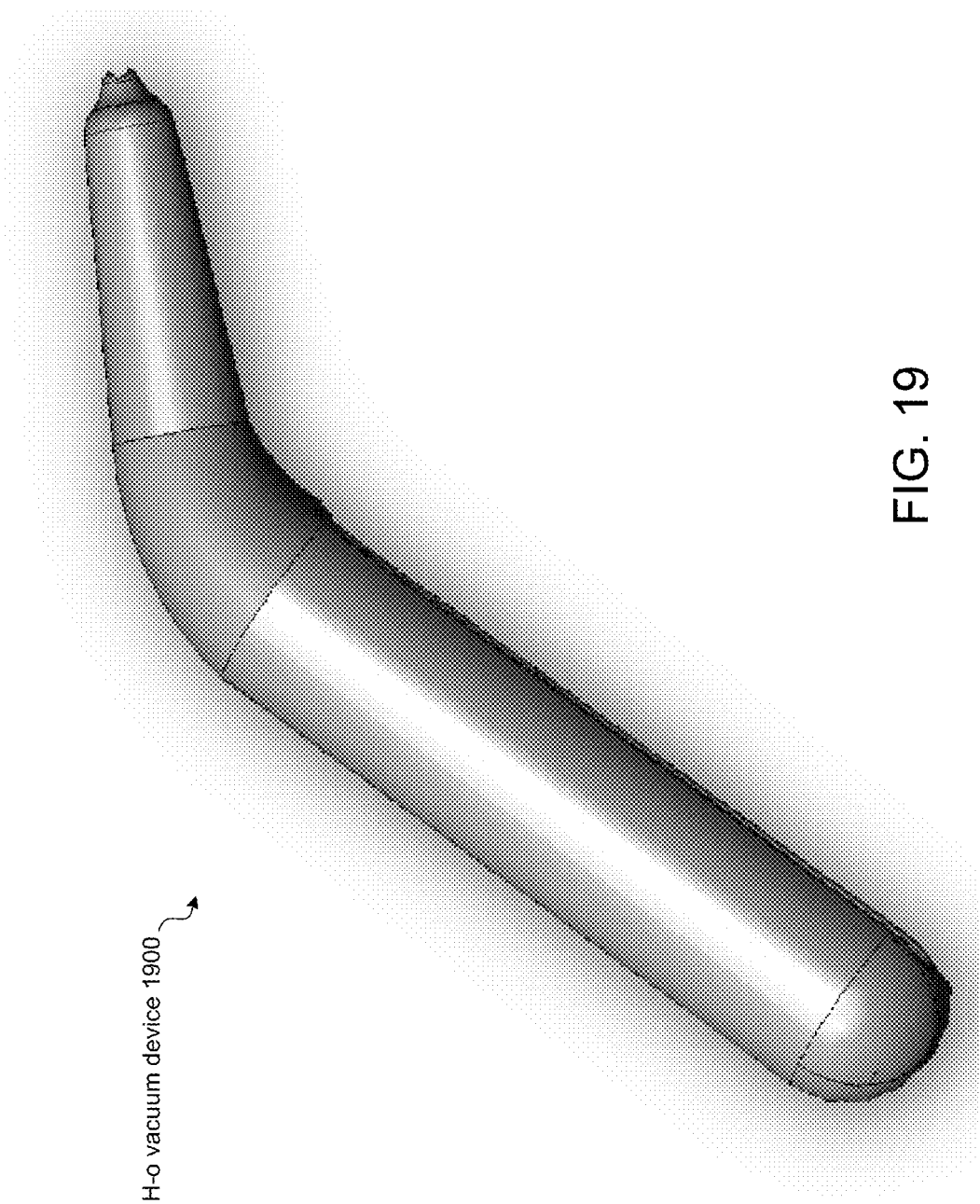

FIG. 19 shows an example hand-operated vacuum device 1900 that can be employed as a nose aspirator, among others.

Figure 20:
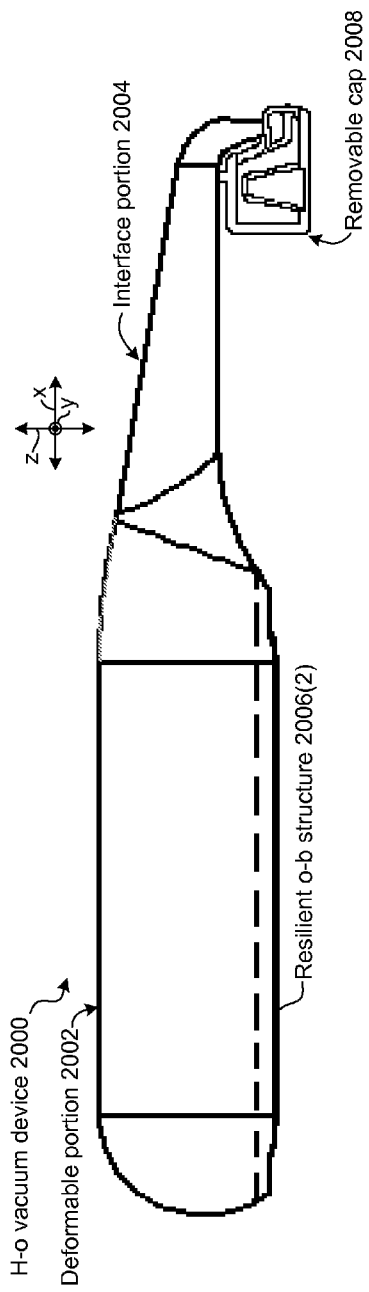
FIGS. 20-21 are elevational views of examples of a hand-operable vacuum device in accordance with some of the present concepts.
Figure 21:
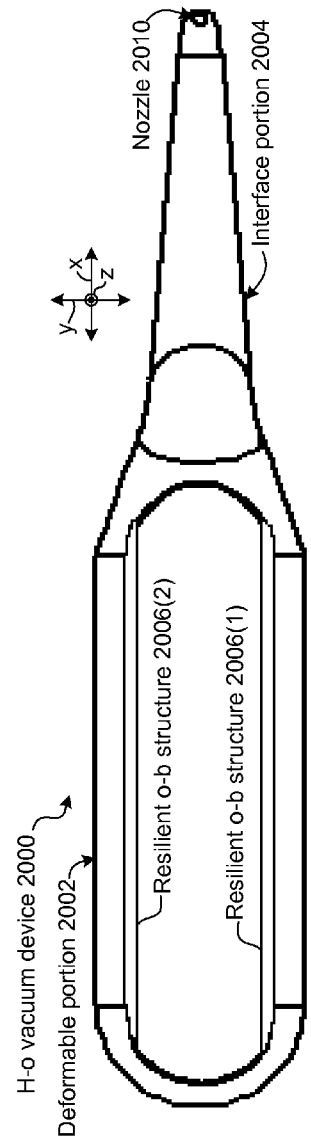

FIGS. 20-21 collectively show another example of a hand-operated vacuum device 2000 that can be employed to various uses. In this case, the hand-operated vacuum device 2000 includes deformable portion 2002 and interface portion 2004. The deformable portion 2002 includes resilient outwardly-biasing structures 2006(1) and 2006(2). The interface portion 2004 includes a removable cap 2008 that covers a nozzle 2010.

FIG. 20 shows the removable cap 2008 in place on the interface portion 2004. FIG. 21 shows the hand-operated vacuum device 2000 with the cap removed to expose nozzle 2010. The removable cap 2008 can be formed during manufacture of the hand-operated vacuum device 2000 and/or added to the hand-operated vacuum device. For instance, the removable cap can be formed as part of the hand-operated vacuum device to help maintain internal conditions of the hand-operated vacuum device. For instance, the removable cap could be utilized to maintain sterile conditions in the hand-operated vacuum device until the cap is removed at the time of use. The user can remove the removable cap, such as by twisting. The user can then squeeze the deformable portion and place the nozzle 2010 near a sample to be collected. The user can reduce and/or release the pressure on the deformable portion to create a vacuum that draws the sample into the hand-operated vacuum device. In some implementations, the removable cap 2008 can be re-installed to maintain the sample and avoid cross-contamination.

In other configurations, the hand-operated vacuum device 2000 can be manufactured and filled with a liquid, such as a wound cleansing antiseptic solution or a mouthwash. The removable cap can then be added to maintain the integrity of the hand-operated vacuum device until use. A user can remove the removable cap and propel the liquid from the nozzle by squeezing the deformable portion 2002.

Hand-operated vacuum devices can be manufactured utilizing various techniques and/or materials. For instance, in some implementations the hand-operated vacuum devices can be formed via a molding process, such as injection molding or blow molding. Various materials can be utilized including but not limited to various polymers. In some cases the hand-operated vacuum devices can be manufactured as a single piece, yet the interface portion can be thicker than the deformable portion so that the interface portion is relatively rigid while the deformable portion is readily deformed by a user. For instance, such a configuration can be achieved by blow molding where the polymer is introduced at the interface end of the hand-operated vacuum device. In one such example, the deformable portion can have an average thickness of 0.1-0.3 millimeters while the interface portion has an average thickness of 0.3-0.6 millimeters.

In summary, hand-operable vacuum devices are described that can allow great vacuum (and/or expulsion) forces to be created by a user. The hand-operable vacuum devices can be inexpensively manufactured and can be disposable and/or reusable. In some instances, the hand-operable vacuum devices can be manufactured and/or packaged so that the devices are sterile until the packaging is opened. Further, the hand-operable vacuum devices lend themselves to construction from materials that can be transparent so that the user can see the contents (if any).

CONCLUSION

Although specific examples of hand-operable vacuum devices are described in language specific to structural features, it is to be understood that the subject matter defined in the appended claims is not intended to be limited to the specific features described. Rather, the specific features are disclosed as exemplary forms of implementing the claimed statutory classes of subject matter.

The invention claimed is:

1. A device, comprising:
an interface portion extending between a nozzle and an elongate deformable portion; and,
the elongate deformable portion extending along an axis, wherein the elongate deformable portion includes at least one longitudinally-oriented resilient structure that extends generally parallel to the axis and inward from a perimeter of the elongate deformable portion,
wherein a user can squeeze the elongate deformable portion into a manipulated configuration to reduce a volume of the device and the at least one longitudinally-oriented resilient structure biases the elongate deformable portion back to a resting configuration that expands the volume of the device.

2. The device of claim 1, wherein the at least one longitudinally-oriented resilient structure comprises a pair of longitudinally-oriented resilient structures.

3. The device of claim 2, wherein the pair of longitudinally-oriented resilient structures extends inward from the perimeter at an angle that is oblique or orthogonal to a proximate portion of the perimeter when the device is in the resting configuration.

4. The device of claim 3, wherein the angle is in a range from about 90 degrees to about 135 degrees.

5. The device of claim 2, wherein the pair of longitudinally-oriented resilient structures is:
generally linear when the elongate deformable portion is in the resting configuration, and
bowed inward when the deformable portion is in the manipulated configuration.

6. The device of claim 1, wherein the interface portion bends away from the axis.

7. The device of claim 1, wherein the nozzle bends away from the axis.

8. A device, comprising:
an interface portion extending between a nozzle and an elongate deformable portion; and, the elongate deformable portion extending along an axis, wherein the elongate deformable portion includes multiple longitudinally-oriented resilient structures that extend generally parallel to the axis and are positioned on one side of the elongate deformable portion, wherein the elongate deformable portion is configured to be squeezed into a manipulated configuration to reduce a volume of the device and the multiple longitudinally-oriented resilient structures bias the elongate deformable portion back to a resting configuration that expands the volume of the device.

9. The device of claim 8, wherein the interface portion bends away from the axis.

10. The device of claim 9, wherein the interface portion bends toward the one side of the elongate deformable portion.

11. The device of claim 8, wherein the nozzle is directed away from the axis.

\* \* \* \* \*